(12) United States Patent
Ye et al.

(10) Patent No.: US 9,295,475 B2
(45) Date of Patent: *Mar. 29, 2016

(54) DRILL BIT LOCKING DEVICE AND DRILL BIT

(75) Inventors: Lei Ye, Chongqing (CN); Jian Zhou, Chongqing (CN); Hua Feng, Chongqing (CN); Fei Li, Chongqing (CN); Hengyang Zhu, Chongqing (CN); Congxiao Li, Chongqing (CN)

(73) Assignee: CHONGQING RUNZE PHARMACEUTICAL CO., LTD., Chongqing (CN)

( * ) Notice: Subject to any disclaimer, the term of this patent is extended or adjusted under 35 U.S.C. 154(b) by 226 days.

This patent is subject to a terminal disclaimer.

(21) Appl. No.: 13/823,095

(22) PCT Filed: Aug. 26, 2011

(86) PCT No.: PCT/CN2011/078964
§ 371 (c)(1),
(2), (4) Date: Mar. 13, 2013

(87) PCT Pub. No.: WO2012/041144
PCT Pub. Date: Apr. 5, 2012

(65) Prior Publication Data
US 2013/0178858 A1    Jul. 11, 2013

(30) Foreign Application Priority Data

Sep. 30, 2010   (CN) .......................... 2010 1 0298086

(51) Int. Cl.
*A61B 17/16* (2006.01)
*B23B 31/00* (2006.01)
*B23B 31/107* (2006.01)

(52) U.S. Cl.
CPC ........... *A61B 17/162* (2013.01); *A61B 17/1615* (2013.01); *B23B 31/005* (2013.01); *B23B 31/1071* (2013.01); *A61B 17/1695* (2013.01); *Y10T 279/17* (2015.01)

(58) Field of Classification Search
CPC ...................................... A61B 17/162
USPC ............................................... 606/80
See application file for complete search history.

(56) References Cited

U.S. PATENT DOCUMENTS

| 5,505,737 | A * | 4/1996 | Gosselin et al. ................. 606/79 |
| 2013/0178856 | A1* | 7/2013 | Ye .......................... A61B 17/162 606/80 |
| 2013/0178857 | A1* | 7/2013 | Ye .......................... A61B 17/162 606/80 |

* cited by examiner

*Primary Examiner* — David Bates

(57) ABSTRACT

A drill bit locking device and a drill bit are provided. The locking device includes a boss with a through hole, a bearing and a support member are arranged an inner wall of a small cylinder above the boss; a locking sleeve is sleeved over the boss, a first bulge is on an inner wall of an upper part of the locking sleeve, and a second bulge is on an inner wall of a lower part; a spring is between the second bulge and an upper bottom surface of the boss; a press plate is threadedly connected with an outer wall of a top part of the small cylinder and presses against the first bulge; holes of different sizes are on the inner wall of the small cylinder and the support member to form a stepped hole, and a steel ball is arranged in the stepped hole.

4 Claims, 1 Drawing Sheet

DRILL BIT LOCKING DEVICE AND DRILL BIT

BACKGROUND OF THE INVENTION

1. Field of the Invention

The present invention relates to a bone drill machine for surgery, and more particularly to a drill bit locking apparatus and a drill bit.

2. Description of the Prior Art

During a surgical operation, skull drills, milling cutters and milling drills are often used to open a skull. The skull drill comprises a main machine, a speed reducer, a locking seat and a drill bit. The drill head comprises a front blade portion and a rear transmission rod. The locking seat is threadedly connected to the front of the speed reducer. The drill head is inserted through the locking seat and connected with the power output of the speed reducer. The function of the locking seat is to engage with the transmission rod, preventing the drill head from disengagement during working. The existing locking apparatus provides engaging hooks to lock. It is inconvenient for installation and not easy for use.

Accordingly, the inventor of the present invention has devoted himself based on his many years of practical experiences to solve these problems.

SUMMARY OF THE INVENTION

The primary object of the present invention is to provide a drill bit locking apparatus and a drill bit for convenient use.

In order to achieve the aforesaid object, the drill bit locking apparatus comprises a boss with a through hole, a bearing arranged on an inner wall of a small cylinder on the boss, a support member to support the bearing, and a locking sleeve fitted on the boss. The locking sleeve has a first bulge arranged on an upper part of an inner wall of the locking sleeve and a second bulge arranged on a lower part of the inner wall of the locking sleeve. A spring is provided between the second bulge and an upper bottom face of the boss. A press plate is threadedly connected to an outer wall of the top part of the small cylinder on the boss and presses the first bulge. Holes of different sizes are arranged on the inner wall of the small cylinder and the support member corresponding in position to the second bulge to form a stepped hole. A steel ball is arranged in the stepped hole.

For fixation of the bearing, the upper bottom face is threadedly connected with a tightening member to hold against the bearing and the support member.

For stable running of the transmission rod, the bit locking apparatus comprises two bearings respectively located under the outer wall and above the tightening member.

For convenient connection of a speed reducer, an inner wall of a big cylinder under the boss has inner threads.

A drill bit to mate with the aforesaid drill bit locking apparatus comprises a front blade portion and a rear transmission rod. The transmission rod has a recess thereon.

When it is necessary to insert the transmission rod, the locking sleeve is pressed down. At this moment, the second bulge disengages from the steel ball. The steel meets the transmission rod to roll outward. After the transmission rod reaches a desired position, the locking sleeve is released. Through the spring, the locking sleeve ascends and the second bulge holds against the steel ball to move inward to engage with the recess of the transmission rod in order to position the transmission rod. The drill head locking apparatus and the drill head are easy and convenient to operate, lock firmly, and offer an improved safety.

DETAILED DESCRIPTION OF THE PREFERRED EMBODIMENTS

Embodiments of the present invention will now be described, by way of example only, with reference to the accompanying drawings.

Figure 1:
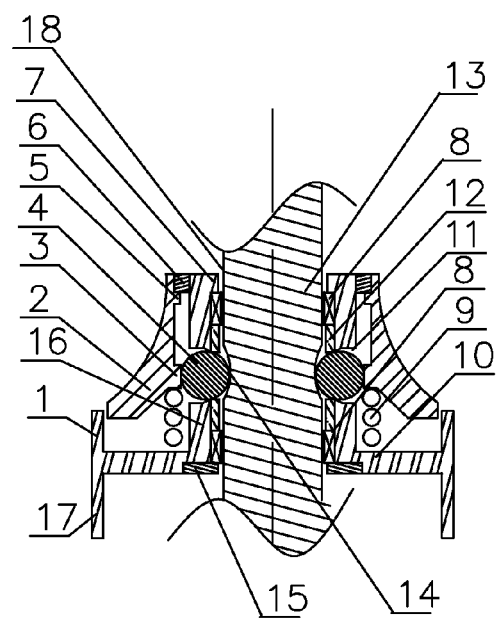
FIG. 1 is a sectional view showing the drill head locking apparatus according to a preferred embodiment of the present invention.
Figure 2:
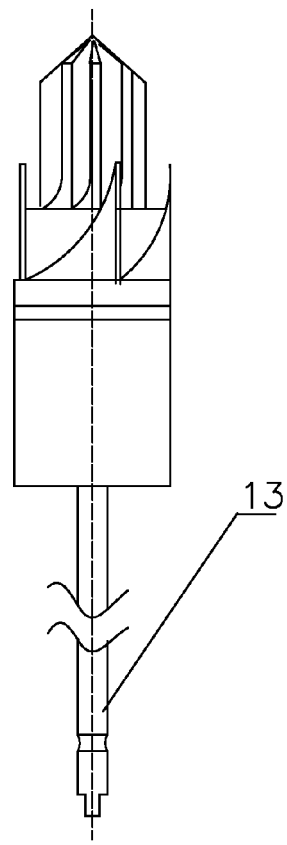
FIG. 2 is a schematic view showing the drill head according to the preferred embodiment of the present invention.

As shown in FIG. 1 and FIG. 2, a drill bit comprises a front blade portion and a rear transmission rod (13). The transmission rod (13) has a recess (14) thereon. A drill head locking apparatus includes a boss (1) with a through hole and a bearing (8) arranged on an inner wall of a small cylinder on the boss (1). In this embodiment, the drill bit locking apparatus comprises two bearings (8) respectively located under an outer wall (7) and above a tightening member (15). A support member (12) is provided between the two bearings (8). An upper bottom face (10) is threadedly connected with the tightening member (15) to hold against the bearings (8) and the support member (12). The two bearings (8) can effectively ensure stability of the transmission rod and decrease heat when rotating. The support member (12) is to enhance firmness of the bearings (8). A locking sleeve (2) is fitted on the boss (1). The locking sleeve (2) has a first bulge (5) arranged on an upper part of an inner wall of the locking sleeve (2) and a second bulge (3) arranged on a lower part of the inner wall of the locking sleeve (2). A spring (9) is provided between the second bulge (3) and the upper bottom face (10) of the boss (1). A press plate (6) is threadedly connected to the outer wall (7) of the top part of the small cylinder on the boss (1) and presses the first bulge (5). Holes of different sizes are arranged on the inner wall of the small cylinder and the support member (12) corresponding in position to the second bulge (3) to form a stepped hole (11). A steel ball (4) is arranged in the stepped hole (11). The hole diameter of the inner wall of the small cylinder is greater than the diameter of the steel ball (4), and the hole diameter of the support member (12) is less than the diameter of the steel ball (4)

The stepped hole (11) corresponds in position to the recess (14) of the transmission rod (13) of the drill bit. An inner wall of a big cylinder under the boss (1) has inner threads. In this embodiment, the number of the stepped holes (11) and the steel balls (4) is two as an equivalent change. The number can be three for a better locking effect.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A drill bit locking apparatus, mating with a drill bit, comprising
   the drill bit, comprising a transmission rod (13) having a recess (14) thereon, with the transmission rod (13) housed through a through hole (18), a boss (1) including a small cylinder (16), a big cylinder (17), and the through hole (18) which opens on two ends thereof,
a steel ball (4),
a press plate (6),
an outer wall (7), disposed next to the transmission rod (13),
one or more spring (9),
an upper bottom face (10),
a stepped hole (11) corresponding, in position and in numbers, to the recess (14), for the locking apparatus to be fixed around the transmission rod (13),
a tightening member (15),
two bearings (8) separately arranged on an inner wall of the small cylinder (16) on the boss (1), each abutting against one of two support members (12),
the two support members (12) separately disposed above and below the steel ball (4) to support the bearings (8),
the locking sleeve (2) having
a first bulge (5) uniformly protruding towards the outer wall (7) and the transmission rod (13) in a same direction on an upper part of an inner wall of the locking sleeve (2), with said first bulge (5) immediately neighboring a press plate (6) above, and
a second bulge (3), abutting against the steel ball (4) by uniformly protruding in the same direction immediately above one or more spring (9), and
the one or more spring (9) being provided between the second bulge (3) and an upper bottom face (10) of the boss (1), through which the locking sleeve (2) ascends and the second bulge (3) holds against the steel ball (4) to move inward in engagement with the recess (14) of the transmission rod (13), in positioning the transmission rod (13),
with the press plate (6) being threadedly connected to the outer wall (7) of a top part of the small cylinder (16) on the boss (1) to press on the first bulge (5),
the stepped hole (11) formed by concentric holes of different diameters, being respectively formed on the inner wall of the small cylinder (16) and the support member (12) neighboring the second bulge (3), such that the small-hole diameter of the small cylinder (16) is greater than a ball diameter of the steel ball (4) to avoid the steel ball (4) falling through the through hole (18) when the transmission rod (13) is removed, and
a support diameter of the support member (12) is less than the ball diameter of the steel ball (4); and
the steel ball (4) being arranged in the stepped hole (11),
wherein the locking sleeve (2) is configured to be pressed down to compress the one or more springs (9) to disengage the steel ball (4) from the second bulge (3) for rolling outwards away from the transmission rod (13) upon meeting the transmission rod (13) in positioning the transmission rod (13);
once the transmission rod reaches a desired position, the locking sleeve (2) is released and the locking sleeve (2) ascends through a restoration force of the one or more springs (9), and the second bugle (3) holds against the steel ball (4) for rolling inwards to engage with the recess (14) of the transmission rod (13).

2. The drill bit locking apparatus as claimed in 1, wherein the upper bottom face (10) is threadedly connected with a tightening member (15) to hold against one of the two bearings (8) and one of the two support members (12).

3. The drill bit locking apparatus as claimed in claim 2, comprising the two bearings (8) respectively located under the outer wall (7) and above the tightening member (15).

4. The drill bit locking apparatus as claimed in one of claims 1 to 3, wherein an inner wall of a big cylinder under the boss (1) has inner threads.

\* \* \* \* \*